(12) United States Patent
Mouradian et al.

(10) Patent No.: US 10,327,649 B1
(45) Date of Patent: *Jun. 25, 2019

(54) NON-INVASIVE WEARABLE BLOOD PRESSURE MONITORING SYSTEM

(71) Applicant: SENSOGRAM TECHNOLOGIES, INC., Plano, TX (US)

(72) Inventors: Vahram Mouradian, Plano, TX (US); Armen Poghosyan, Yerevan (AM)

(73) Assignee: Sensogram Technologies, Inc., Plano, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/254,880

(22) Filed: Sep. 1, 2016

Related U.S. Application Data

(63) Continuation-in-part of application No. 14/675,639, filed on Mar. 31, 2015.

(60) Provisional application No. 62/252,561, filed on Nov. 8, 2015, provisional application No. 62/213,097, filed on Sep. 1, 2015, provisional application No. 61/973,035, filed on Mar. 31, 2014.

(51) Int. Cl.
| | | |
|---|---|---|
| *A61B 5/05* | (2006.01) | |
| *A61B 5/021* | (2006.01) | |
| *A61B 5/026* | (2006.01) | |
| *A61B 5/00* | (2006.01) | |

(52) U.S. Cl.
CPC ......... *A61B 5/02108* (2013.01); *A61B 5/026* (2013.01); *A61B 5/6801* (2013.01)

(58) Field of Classification Search
CPC . A61B 5/02108; A61B 5/7278; A61B 5/0082; A61B 2576/00; A61B 2562/0238; A61B 2560/0475; A61B 5/6801; A61B 5/026; A61B 2560/0223

USPC ................................................. 600/473–480
See application file for complete search history.

(56) References Cited

U.S. PATENT DOCUMENTS

| | | | |
|---|---|---|---|
| 4,781,195 A | 11/1988 | Martin | |
| 5,713,355 A | 2/1998 | Richardson et al. | |
| 5,846,190 A | 12/1998 | Woehrle | |
| 5,885,213 A | 3/1999 | Richardson et al. | |
| 5,954,644 A | 9/1999 | Dettling et al. | |
| 6,385,471 B1 | 5/2002 | Mortz | |
| 6,491,647 B1 * | 12/2002 | Bridger ............... | A61B 5/021 128/900 |
| 7,384,398 B2 | 6/2008 | Gagnadre et al. | |
| 7,616,110 B2 | 11/2009 | Crump et al. | |
| 7,740,591 B1 | 6/2010 | Starr et al. | |

(Continued)

FOREIGN PATENT DOCUMENTS

| | | |
|---|---|---|
| WO | 0143624 A2 | 6/2001 |
| WO | 2008109185 A2 | 9/2008 |
| WO | 2016150749 A1 | 9/2016 |

OTHER PUBLICATIONS

Addison et al., "Developing an algorithm for pulse oximetry derived respiratory rate (RRoxi): a healthy volunteer study", J. Clin. Monit Comput, 2012, vol. 26, pp. 45-51.

(Continued)

*Primary Examiner* — Sanjay Cattungal
(74) *Attorney, Agent, or Firm* — RatnerPrestia

(57) ABSTRACT

Presented are embodiments of an apparatus and methodology for non-invasive, continuous or semi-continuous monitoring of human blood pressure by photoplethysmography (PPG) based sensor system.

9 Claims, 10 Drawing Sheets

(56) References Cited

U.S. PATENT DOCUMENTS

| | | | |
|---|---|---|---|
| 7,827,011 | B2 | 11/2010 | De Vaul et al. |
| 8,036,842 | B2 | 10/2011 | DeVaul et al. |
| 8,313,439 | B2 | 11/2012 | McCombie et al. |
| 8,378,811 | B2 | 2/2013 | Crump et al. |
| 8,618,930 | B2 | 12/2013 | Papadopoulos et al. |
| 8,866,606 | B1 | 10/2014 | Will et al. |
| 9,135,699 | B2 | 9/2015 | Ralovich et al. |
| 9,396,645 | B2 | 7/2016 | Will et al. |
| 9,489,815 | B2 | 11/2016 | TenKate |
| 9,526,421 | B2 | 12/2016 | Papadopoulos et al. |
| 9,547,977 | B2 | 1/2017 | Will et al. |
| 9,640,057 | B1 | 5/2017 | Ross |
| 9,704,154 | B2 | 7/2017 | Xing et al. |
| 9,773,397 | B2 | 9/2017 | Ten Kate et al. |
| 2004/0044290 | A1* | 3/2004 | Ward ............... A61B 5/022 600/490 |
| 2009/0105556 | A1* | 4/2009 | Fricke ............... A61B 5/0059 600/301 |
| 2010/0016738 | A1 | 1/2010 | Addison et al. |
| 2012/0078116 | A1 | 3/2012 | Yamashita |
| 2014/0142460 | A1 | 5/2014 | Zhang et al. |
| 2015/0164352 | A1 | 6/2015 | Yoon et al. |
| 2016/0038044 | A1 | 2/2016 | Banerjee et al. |
| 2016/0038061 | A1 | 2/2016 | Kechichian et al. |
| 2016/0174913 | A1 | 6/2016 | Somanath et al. |
| 2016/0213314 | A1 | 7/2016 | Zuckerman-Stark et al. |
| 2016/0360971 | A1 | 12/2016 | Gross et al. |
| 2017/0027511 | A1 | 2/2017 | Conner |
| 2017/0172463 | A1 | 6/2017 | Papadopoulos et al. |

OTHER PUBLICATIONS

Image of Sensotrack, downloaded Sep. 25, 2016, 1 page.
Meredith et al., "Photoplethysmographic derivation of respiratory rate: a review of relevant physiology", Journal of Medical Engineering & Technology, 2012, pp. 60-66.
George et al., "Respiration Rate Measurement From PPG Signal Using Smart Fusion Technique", International Conference on Engineering Trends and Science & Humanities, 2015, 5 pages.
Burns, "Senso Track Monitors Biometric Health Through Your Ear", downloaded http://www.slashgear.com/sensotrack-monitors-biometric-health-through-your-ear-22351940, Sep. 25, 2016, 8 pages.
Lazaro et al., "Deriving respiration from photoplethysmographic pulse width", Med. Bio. Eng. Comput., 2013, vol. 51, pp. 233-242.
Notice of Allowance for U.S. Appl. No. 15/344,467, dated Jul. 9, 2018, 18 pages.
Notice of Allowance for U.S. Appl. No. 14/675,639, dated Jul. 16, 2018, 9 pages.
International Search Report and Written Opinion for International Application No. PCT/US18/18159, dated May 7, 2018, 7 pages.

* cited by examiner

NON-INVASIVE WEARABLE BLOOD PRESSURE MONITORING SYSTEM

CROSS REFERENCE TO RELATED AND PRIORITY APPLICATIONS

This application claims the benefit of U.S. application No. 62/213,097 entitled CONTINUOUS NON-INVASIVE WEARABLE BLOOD PRESSURE MONITORING SYSTEM, filed on Sep. 1, 2015. This application also claims the benefit of U.S. application No. 62/252,561, entitled CONTINUOUS NON-INVASIVE WEARABLE BLOOD PRESSURE MONITORING SYSTEM, filed on Nov. 8, 2015. This application is also a continuation in part of the commonly-owned U.S. application entitled "CONTINUOUS NON-INVASIVE WEARABLE BLOOD PRESSURE MONITORING SYSTEM," application Ser. No. 14/675,639, Filed on Mar. 31, 2015, which claims priority to U.S. provisional patent application Ser. No. 61/973,035, filed on Mar. 31, 2014, the disclosures of all of the above are incorporated herein by reference for all purposes.

TECHNICAL FIELD

The invention relates in general to photoplethysmographic (PPG) measurement systems and apparatuses using optical sensors, and in particular to non-invasive continuous human blood pressure measurement by wearable optical sensing systems.

BACKGROUND INFORMATION

Blood pressure measurement techniques are generally put in two broad classes: instant and continuous. Instant techniques of blood pressure measurement, involve some kind of sensor working for a short period of time, such as cuff (non-invasive) or catheter (invasive) out of which an instant blood pressure data is derived. The continuous techniques allow of measurement of blood pressure values continuously for a defined period of time, with improved patient comfort and safety, but usually at the expense of accuracy.

Photoplethysmography or photoplethysmographic (PPG) systems have been used in an attempt to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Attempts at measuring some of these characteristics have used of a non-invasive sensor which scatters light through a portion of the patient's tissue where blood is perfused through the tissue, and optically senses the absorption of light in such tissue. This is a good candidate for the continuous blood pressure monitoring.

Typically PPG measurement systems include an optical sensor for an attachment to the tip of patient's appendage (e.g., a finger, earlobe and others). The sensor directs light signals into the appendage where the sensor is attached. Some portion of light is absorbed and a remaining portion passes through patient tissue. The intensity of the light passing through the tissue is monitored by the optical sensor. The intensity related signals produced by the sensor are used to compute blood parameters based on blood flow—such as the heart rate.

However to date, such techniques have not been used for the blood pressure determinations. What is needed, therefore, is a blood pressure measurement apparatus and process that is continuous, non-invasive and accurate.

SUMMARY

In response to these and other problems, there is disclosed a blood pressure monitoring system and method using a non-invasive device and method of monitoring blood pressure. More particularly, aspects of the present invention may be a wearable non-invasive blood pressure (NIBP) monitor allowing a mobile and remote reading of blood pressure data from the close proximity as well as from the remote location via an Internet connection.

Also disclosed are aspects that include the sub-systems to calibrate the system to the individual user to increase the accuracy and validity of the data.

One advantage with certain embodiments of this invention is the ability of the system to calibrate and measure the blood pressure without any invasive equipment, allowing a comfortable wearing by the patients.

These and other features, and advantages, will be more clearly understood from the following detailed description taken in conjunction with the accompanying drawings. It is important to note that the drawings are not intended to represent the only aspect of the invention.

DETAILED DESCRIPTION

Specific examples of components, signals, messages, protocols, and arrangements are described below to simplify the present disclosure. These are, of course, merely examples and are not intended to limit the invention from that described in the claims. Well-known elements are presented without detailed description in order not to obscure the present invention in unnecessary detail. For the most part, details unnecessary to obtain a complete understanding of the present invention have been omitted in as much as such details are within the skills of persons of ordinary skill in the relevant art. Details regarding control circuitry used to control of the various elements described herein are omitted, as such control circuits are within the skills of persons of ordinary skill in the relevant art.

Figure 1:
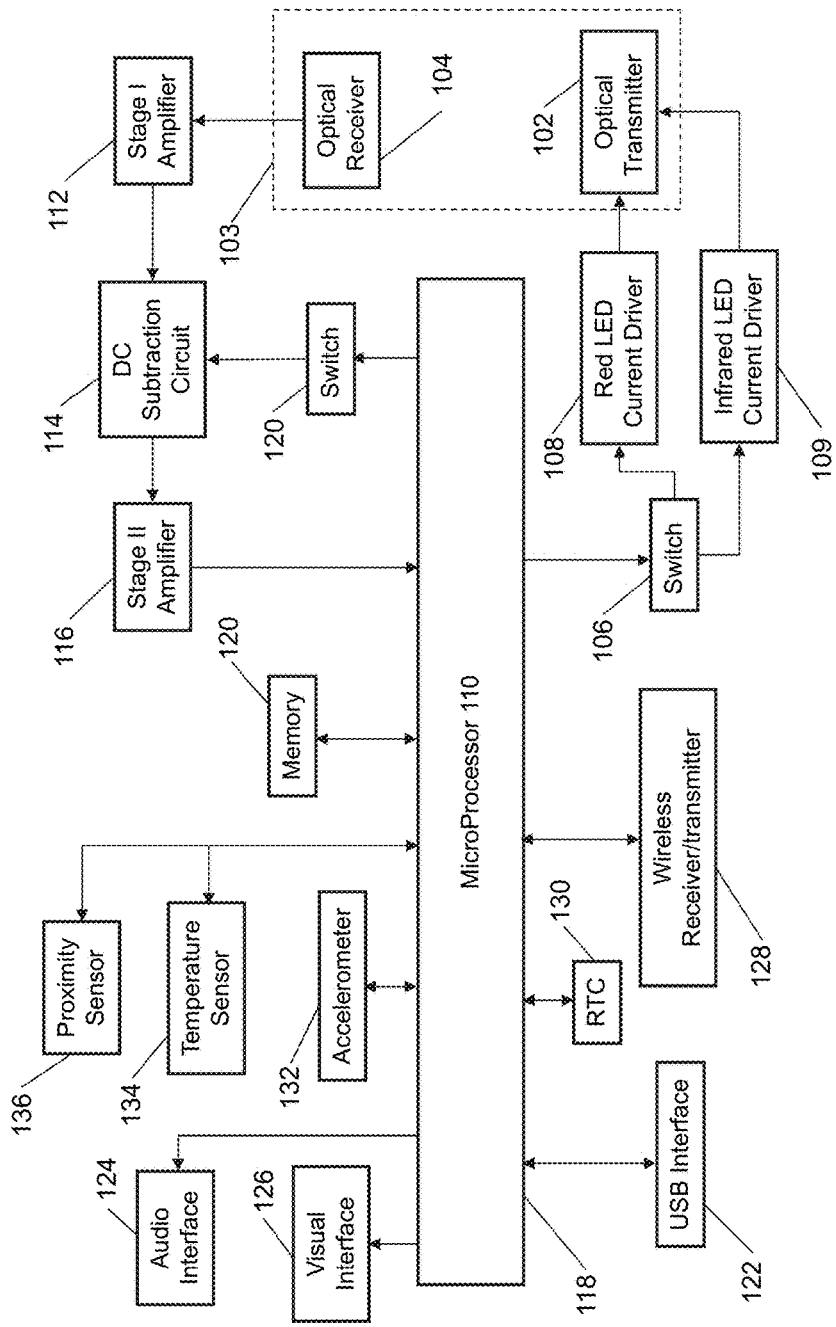
FIG. 1. is a conceptual functional diagram of a vital signs monitoring system.

FIG. 1 illustrates a conceptual functional diagram of a vital signs monitoring system 100. The system 100 includes an optical sensor subsystem or pulse oximeter system 103. The optical sensor subsystem 103 is designed to assist in the measurement of a user's vital signs, such as blood pressure, heart rate, respiration rate and oxygen saturation, by using non-invasive methods. For instance, absorption of light by oxyhemoglobin and deoxyhemoglobin are significantly different at red light and infrared light. By measuring the difference in absorbance at various wavelengths, the degree of blood oxygen saturation can be estimated.

The optical sensor subsystem 103 is positioned on a portion of the user's tissue. For instance, the optical sensor subsystem 103 may be mounted on a finger, ear lobe, or a wrist (in a watch worn by the user). The optical sensor subsystem 103 includes an optical transmitter 102, which is designed to transmit light at predetermined wavelengths and an optical receiver 104, adapted to receive the transmitted light from the optical transmitter 102.

In certain embodiments, the optical transmitter 102 and the optical receiver 104 are positioned adjacent to each other so that the optical receiver 104 may receive reflected light from the user's tissue originated by the optical transmitter 102. In other words, the optical transmitter transmits light to penetrate the skin to the blood underneath. Some portion of transmitted light is absorbed by the blood, and the remaining portion of it is reflected by the tissue, which is then received by the optical receiver 104.

In other embodiments, the optical receiver 104 is positioned in opposition to the optical receiver 102 such that the optical receiver 104 may receive light that has passed through the tissue and goes through the blood (such as when the user's ear lobe is positioned between the optical receiver 102 and the optical receiver 104.)

The intensity of light passing through the tissue is received by the optical receiver 104, which in some embodiments, may be a photodiode. The photodiode generates current from the received light. The greater the light received, the greater the current generated by the photodiode.

The light to be transmitted through the user's tissue is selected to be of one or more wavelengths that are absorbed by the blood in an amount representative of the amount of the blood constituent present in the blood vessel. The amount of transmitted light scattered through or reflected from the tissue will vary in accordance with the changing amount of blood constituent in the blood vessel and the related light absorption.

In certain embodiments, the optical transmitter 102 transmits red light at around a wavelength of 580 to 660 nm via a red LED, and infrared light at around a wavelength range of 880 to 940 nm via an infrared LED. Thus, in certain embodiments the optical transmitter 102 comprises two LEDs controlled by a LED controller circuit. In certain embodiments, the LED controller circuit selects the active LED and controls its current management. In the illustrative embodiment, the LED controller circuit comprises a Digital-to-Analog Converter ("DAC"), a switch 106, a Red LED current driver 108, and an Infrared LED current driver 109. Switching to the active LED may be controlled by a microprocessor 110 via MCU pins, which commutes control voltage from a Digital to Analog Converter ("DAC") (not shown) to the selected LED at appropriate intervals via the switch 106 and the LED current drivers 108 and 109. As is well known in the art, a DAC converts digital signals to an analog signal such as current or voltage. Such digital signals are usually called PPG signals.

In embodiments that use a single photodiode, the light of different wavelengths, such as red and infrared, may be time multiplexed. The detected signal, therefore, should be demultiplexed. The demultiplexing frequency may be high enough so that it is much larger than the pulse rate.

In certain embodiments, the current generated by the optical receiver 104 may be sent to a first stage amplifier 112 to amplify the received current, such as a first stage transimpedance amplifier. The amplified current or output signal from the first stage amplifier 112 comprises a DC component and an AC component. The AC component represents the change of received light (by the optical receiver 104) and thus the change of blood in the vessel. Also the physiological, ambient and system generated noise is present in the received light as a DC component, in other words the blood change in the vessel can be visualized in the form of an AC component accompanied by the noise represented in the form of the DC component. At this stage, only the AC component is the subject of processing.

In some embodiments, a DC subtraction circuit 114 extracts the DC component of the signal and is used as an offset input to the second stage operational amplifier 116. Thus, only the AC portion of the signal is amplified by the second stage amplifier 116.

An A/D converter (not shown) receives the amplified current from the second stage operational amplifier 116 and converts it into a digital waveform which is then sent to the microprocessor or microcontroller 110.

In certain embodiments, the system 100 also includes an ambient noise reduction circuit, which reduces noise due to ambient light effect in the received current using the switch 120. More details regarding the ambient noise reduction circuit is found in the jointly owned and co-pending patent application "Apparatus for Ambient Noise Cancellation in PPG Sensors," application Ser. No. 14/674,499, filed on Mar. 31, 2015, the specification of which has been incorporated by reference into this Application.

The microprocessor 110 receives the digital waveform from the Second Stage Amplifier 116 via the A/D converter as an input signal. Although many microprocessors may be used, an ultra-low power microprocessor may be preferred for power efficiency and battery life reasons. In one embodiment, the microprocessor 110 or "MCU" may be based on the 32 bit ARM Cortex-M4 core, which includes a variety of peripheral devices. In certain embodiments, the microprocessor is ultra low power with a power consumption of about 238 µA/MHz in dynamic run mode, and approximately 0.35 µA in lowest power mode. Although low energy, the core of the microprocessor 110 is powerful enough to allow collection and processing of data from the sensors on the fly.

The microprocessor 110 is coupled to at least one memory 120 for storing post-processed data and for the firmware instructions. In certain embodiments, the memory 120 may be approximately 256 Mb of serial flash memory. In certain embodiments, the microprocessor 110 is also in communication with a USB ("Universal Serial Bus") interface 122, such as a micro USB interface. The USB interface 122 may be coupled to an USB-to-UART ("Universal Asynchronous Receiver and Transmitter") converter (not shown), such as an enhanced UART with an USB interface. Among other features, the USB interface 122 allows the microprocessor 110 to communicate with an external computing device via a wired USB cable. In certain embodiments, the USB interface 122 also supports USB suspend, resume and remote wakeup operations. Program instructions residing in the memory 120 may be updated via the USB interface 122 (e.g., firmware) and where necessary data may be transferred between the microprocessor 110 and the computing device.

The USB interface 122 is also coupled to the system's power supply circuit (not shown) and can receive direct current to charge and recharge a portable power supply, such as a lithium-ion polymer battery (not shown). In some embodiments, the power supply may be coupled to an On/Off controller which is also coupled to an on/off switch. In certain embodiments, the system's power supply can be inductively charged. As such power supply circuits are well known in the art, the power supply circuit will not be discussed in detail in this disclosure.

In certain embodiments, the microprocessor 110 sends control signals to the optical transmitter 102 via the switch 106 as described above. In turn, the optical transmitter 102 begins transmitting light to be received by the optical receiver 104 to start the data gathering process. Additionally, the microprocessor 110 performs data acquisition and analysis on the received digital waveforms from the second stage amplifier 116 (described above). As will be described below, the microprocessor 110 uses the received digital waveforms to determine calculated results such as blood pressure, heart rate, oxygen saturation, and respiratory rate. The calculated results may be stored in the memory 120 for later transmission or use. The calculated results may also be sent to a number of user interface devices. For example, in certain embodiments, the calculated results may be sent to an audio interface 124 such as an earphone speaker. In other embodiments, the calculated results may be sent to a visual interface 126, such as an LCD display or touch sensitive screen via a display driver (not shown).

Additionally, the calculated results may also be sent to a wireless transceiver 128. In certain embodiments, the wireless transceiver 128 may be a Bluetooth radio capable of communication with a smart phone or other such Bluetooth capable computing device. In certain embodiments, the Bluetooth radio may be a low energy "System on a chip" or "SOC." The SOC may include a microcontroller core with Flash memory and Static RAM. In certain embodiments, the SOC also includes a Bluetooth v4.0 low energy front-end. In certain embodiments, the SOC may be used as a Network processor, which provides Bluetooth Low Energy connectivity. In other embodiments, a ZIGBEE protocol or any other point-to-point wireless protocol (standard or non-standard) may be incorporated into the wireless transceiver.

The microprocessor 110 may also be connected to a number of other system components and peripherals. In certain embodiments, the components may include a Real Time Clock or "RTC" 130, an accelerometer/gyroscope 132, a temperature sensor 134, and/or a proximity sensor 136.

In certain embodiments, a real time clock 130 may be a RTC module with built-in crystal oscillating at 32.768 kHz, 1 MHz Fast-mode Plus (Fm+) two wire I2C interface. In certain embodiments, such an RTC module may have the following characteristics: a wide interface operating voltage; 1.6-5.5 V, Wide clock operating voltage: 1.2-5.5 V and; ultra low power consumption—130 nA typ @ 3.0V/25° C.

In certain embodiments, the accelerometer/gyroscope 132 may be an intelligent, low-power, 3/6/9-axis accelerometer/gyroscope with 12 bits of resolution. In certain embodiments, the accelerometer may be provided with embedded functions with flexible user-programmable options, configurable to two interrupt pins. For instance, embedded interrupt functions enable overall power savings, by relieving the host processor from continuously polling data. There may be access to either low-pass or high-pass filtered data, which minimizes the data analysis required for jolt detection and faster transitions. In certain embodiments, the accelerometer 132 may be configured to generate inertial wake-up interrupt signals from any combination of the configurable embedded functions, enabling the accelerometer/gyroscope 132 to monitor inertial events while remaining in a low-power mode during periods of inactivity.

In certain embodiments, the temperature sensor 134 may be a digital output temperature sensor in a four-ball wafer chip-scale package (WCSP) capable of reading temperatures to resolution of 1° C. In certain embodiments, the temperature sensor 134 has a two-wire interface that compatible with both I2C and SMBus interfaces. In addition, the interface supports multiple devices on the bus simultaneously, eliminating the need to send individual commands to each temperature sensor on the bus. In certain embodiments, the voltage requirements vary between 1.4V to 3.6V.

In some embodiments, the proximity sensor 136 allows the presence of a nearby object to be detected. The proximity sensor 136 may be a self-contained, self calibrating digital IC which projects a touch or proximity field to several centimeters through any dielectric. Certain embodiments may be coupled to a capacitor for operation.

Figure 9A:
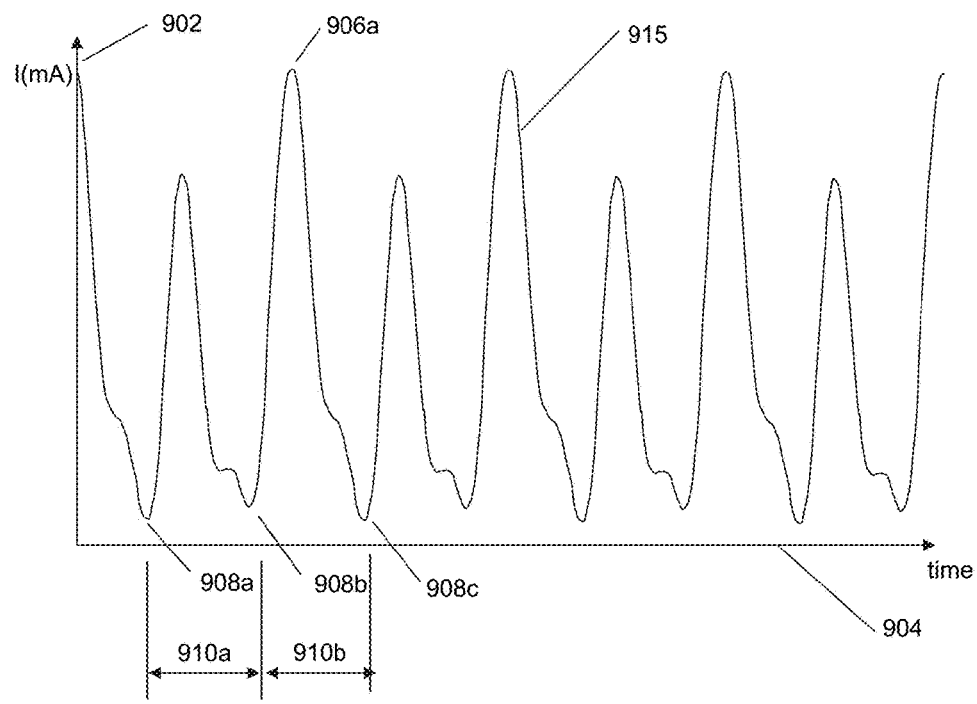
FIG. 9A is an illustrative representative graph of a series of PPG sensor values (y axis) plotted against time (x axis).

A program application or process in the memory 120 may be executed by the microprocessor 110 which in conjunction with the PPG sensor system 103 can estimate certain physical conditions of the user. For instance, the system 100 can measure blood flow. Because the blood flow is pulsatile in nature, the transmitted light (and the value of the PPG signal from optical sensor) changes with time. Over time, the strength of the received PPG signal (usually current or voltage) can be plotted against time when enough samples are taken. A representative plot for a series of PPG sensor values vs. time is illustrated in FIG. 9A. The derived PPG signal curve (after amplification and analog-digital conversion of initial photodiode signal) may then be subjected to mathematical and numerical transformation processes performed by the microcontroller 110 (filtering, normalization, signal conditioning, removal of DC components, etc.) to increase the signal accuracy (and therefore, the accuracy of the PPG curve).

An exemplary PPG signal curve 915 is illustrated in FIG. 9A which illustrates the current (or blood flow) represented on the y axis 902) graphed against a particular period of time (x axis 904). Once the PPG signal curve 915 has been received for a particular amount of time (t), with the help of a peak and valley curve detector processes (described below), the signal period can be measured, the inverse value of which is related to the heart rate. For instance, a peak of the plotted PPG signal, such as peak 906a on the signal curve 915, corresponds to high point of blood flow through the tissue. Similarly, a "foot," such as foot 908a, corresponds to the low point of blood flow through the tissue. As is known, a single pulse represents the rhythmic dilation of the arteries resulting from the beating of the heart. Thus, a single pulse corresponds to the time between peaks or foots (or other recurring events) in the signal curve 915 of FIG. 9A. For purposes of illustration, the first single pulse or pulsation 910a can be illustrated as the time between the first foot 908a and the second foot 908b. The second pulse or pulsation 310b can be defined as the time between the second foot 908b and the third foot 908c and so on. The pulse rate or heart rate is typically defined as the number of pulsations measured within a minute.

Of course, the graph of FIG. 9A may be represented in memory 120 by a table or array of received PPG values. For instance, one table may comprise:
1. Index (j),
2. Time (HH:SS:MS (j)),
3. Pulse (i),
4. Signal PhS(i,j).

In certain situations, the signal curve 915 can be modeled as a function representing a basic model for human blood flow measured close to the heart as an RLC series circuit. Certain characteristics of such a model can be represented generally from the following equation (1):

$$\frac{du}{dt} = R\frac{di}{dt} + L\frac{d^2i}{dt^2} + \frac{i}{C} \quad (1)$$

where: u is voltage or blood pressure,
t is time
i is current from the PPG data;
R is the vascular or peripheral resistance at the point of measurement;
L is the inductance which correspondences to inertia of the blood, and
C is the compliance.

Compliance or "C" relates to the elasticity of arteries within a user (e.g., a measure of how easily an artery can be stretched or distend). An artery with high compliance value can be stretched easily. Arterial compliance may be defined as the change in volume stored per change in internal pressure (Compliance=Volume/Pressure) which is not constant but depends on the blood pressure in a nonlinear relationship. Arteries with high compliance can accommodate large amount of blood with only small increase in systolic pressure. A person's compliance value often decreases with age.

"R" relates to the vascular resistance ("VR") of the user at the point of measurement, and "L" relates to the viscosity of the user's blood, which is an indication of the inertia or movement of the blood of the user. Thus, equation (1) above can be represented by a curve or graph and correlated to the PPG signal curve 315 illustrated in FIG. 9A.

Blood pressure is also related to a blood flow equation (2). The blood pressure function curve (2) may be found by integrating both sides of equation (1), which yields:

$$u = \int \left( R\frac{di}{dt} + L\frac{d^2i}{dt^2} + \frac{i}{C} \right) dt \quad (2)$$

Figure 9B:
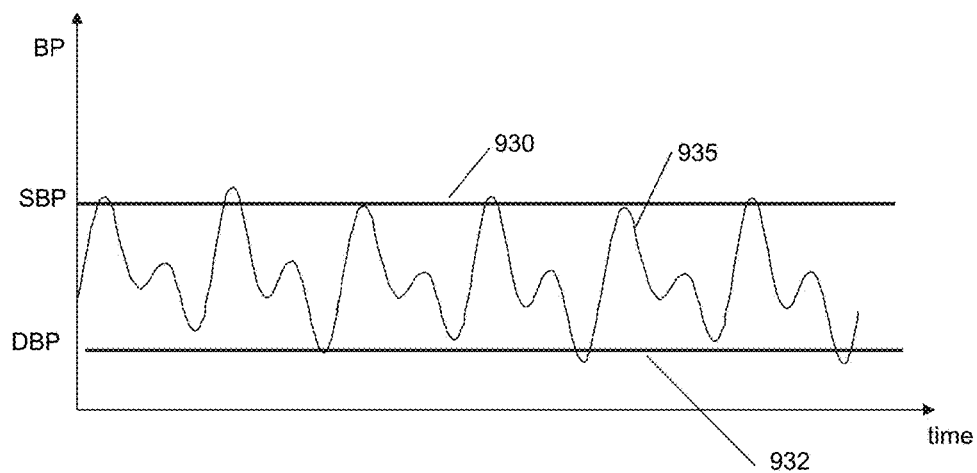
FIG. 9B is an illustrative representative graph of a user's blood pressure (y axis) plotted against time (x axis).

When all of the coefficients are known, equation (2) can also be represented by a curve or a graph plotted over time, such as a blood pressure curve 935 illustrated in FIG. 9B which represents a user's blood pressure over a given period of time (t). As illustrated in FIG. 9B, the curve 935 also has peaks. The line 930 generally corresponds to the series of peaks of the curve 935 and is known as the systolic blood pressure ("SBP"). The SBP relates to the pressure in the arteries when the heart beats (the hear muscle contracts). In contrast, the line 932 generally corresponds to the series of valleys of the curve 935 and is known as the diastolic blood pressure ("DBP"). The DBP relates to the pressure in the arteries between heart beats (when the heart muscle is resting and refilling with blood).

Figure 2:
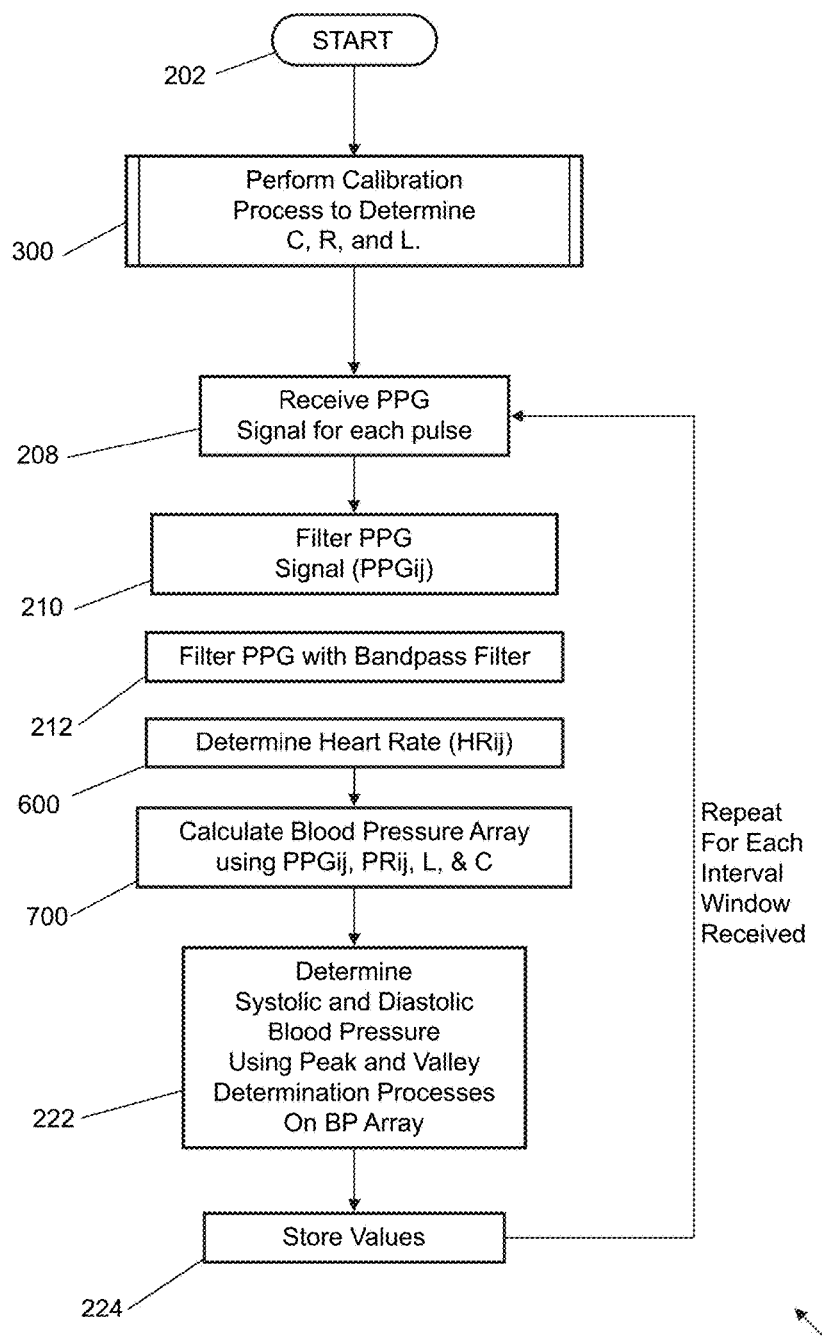
FIG. 2 is a flowchart representing an overall process which may be implemented by the vital signs monitoring system of FIG. 1.

FIG. 2 is a process flow chart illustrating an overall process 200 which may be used with certain aspects of the present invention. The basic process 200 starts at step 202 and continues to step 300.

In step 300, a device calibration process is executed to determine values of coefficients used in equations (1) and (2) above, such as R "vascular resistance", L "viscosity of the blood", and C "compliance" for an individual user. In certain embodiments, R, L and C vary with each person and may be determined based on user-specific information as explained below. Default values of these parameters are used for the initial estimations of the blood pressure, and the values get changed as a result of the numerical methods used in the calibration process.

As will be explained below, during the device calibration process, a user's blood pressure is measured with the aid of an external blood pressure measuring device. After the calibration process is performed, the system 100 usually does not need to be recalibrated unless physiological changes occur in the user's body, which may affect the values of C, L, or R.

In certain embodiments, step 300 performs sub-processes to determine the values for the coefficients C, L, and R for the individual user. In other embodiments, step 300 performs sub-processes to determine C and L for an individual user while R is determined from empirical analyses of typical users.

Once the calibration process 300 determines values for C, R, and L as will be described below, in step 208, a new series of PPG data points or signals may be received from the PPG optical sensor 104 (FIG. 1) for processing.

Sampling of data from the PPG system or sensor then takes place. In certain embodiments, 512 samples of data points per second from the PPG sensor are received and stored in a PPG data array. In certain embodiments, a moving "analysis window" is providing in the array so that previous data points can be used to perform the required analysis. For instance, a predetermined number of data points or cells in an array are provided to a derivative function so that slopes of the PPG signal may be determined. In certain embodiments, the raw PPG signal is processed through an ambient noise cancellation circuit described above to produce a modified PPG signal or signal curve. Thus, filtered and quantized PPG data is received by the processor in step 210. In certain embodiments, quantization is the result of sampling in the hardware ADC. Although the sampling is performed by firmware routines, in certain embodiments, the process of quantizing an analog signal into a sample is done by the hardware of the system 100 discussed above.

In step 212, the modified PPG signal may be filtered through the equivalent of a band pass filter, which in certain embodiments is a low pass filter used in conjunction with a high pass filter to remove noise and other artifacts. In certain embodiments, the data points are processed through the equivalent a 0.5 to 4 Mhz bandpass filter to remove noise and extraneous artifacts to create a Q Array or PPG data array (e.g., a set of data cells to hold filtered PPG values in memory 120).

In certain embodiments, the filtered PPG(ij) or Q signal may be stored in a table along with the following data:
1. Index (j),
2. Time (HH:SS:MS (j)),
3. Pulse (i),
4. Signal PhS(i,j).

Step 600 determines the Heart Rate for the user. Recall from FIG. 9A, that the Q data or signal is cyclic in nature.

Thus, any number of peak detection and/or valley detection methods may be used to calculate the pulse widths 910 (FIG. 9). Once the pulse width has been determined, the heart rate can readily be calculated. Details regarding the Heart Rate determination process 600 is discussed below in reference to FIG. 6.

In step 700, a blood pressure estimation process may be implemented to estimate the user's blood pressure curve (which can be stored as a blood pressure array or function). Details regarding the blood pressure estimation process 700 are discussed below in reference to FIG. 7. Generally, however, the instantaneous blood pressure ("u") can be calculated using values from the PPG signal curve (i), and the previously determined values for R, L C (from step or process 300) to compute the continuous blood pressure according to equation (2):

$$u = \int \left( R\frac{di}{dt} + L\frac{d^2i}{dt^2} + \frac{i}{C} \right) dt \qquad (2)$$

In step 222, a peak and valley determination processes can be performed on the continuous blood pressure blood pressure array or function to determine the Systolic and Diastolic blood pressure for the user.

In step 224, the Systolic and Diastolic blood pressure values may then be transmitted to a user interface or stored in the memory 120 (FIG. 1) for additional processing and reporting.

In some embodiments, a continuous or near continuous BP measurement process may be performed. In such embodiments, the process at step 224 then flows back to step 208 where a new set of PPG signal is received and the process flows to step 210 where the steps 210 through 216 are continuously repeated for as long as the device is on and/or gathering PPG signals. In other embodiments, the BP measurement process is only performed at predetermined intervals.

As discussed above, the calibration sub-process 300 is usually implemented once for a particular user to determine basic coefficient values for R, L, and C for an individual user. Once the basic coefficient values have been determined, there is usually no need to rerun the calibration process unless the physiological changes in the user has occurred since the last calibration.

Figure 3:
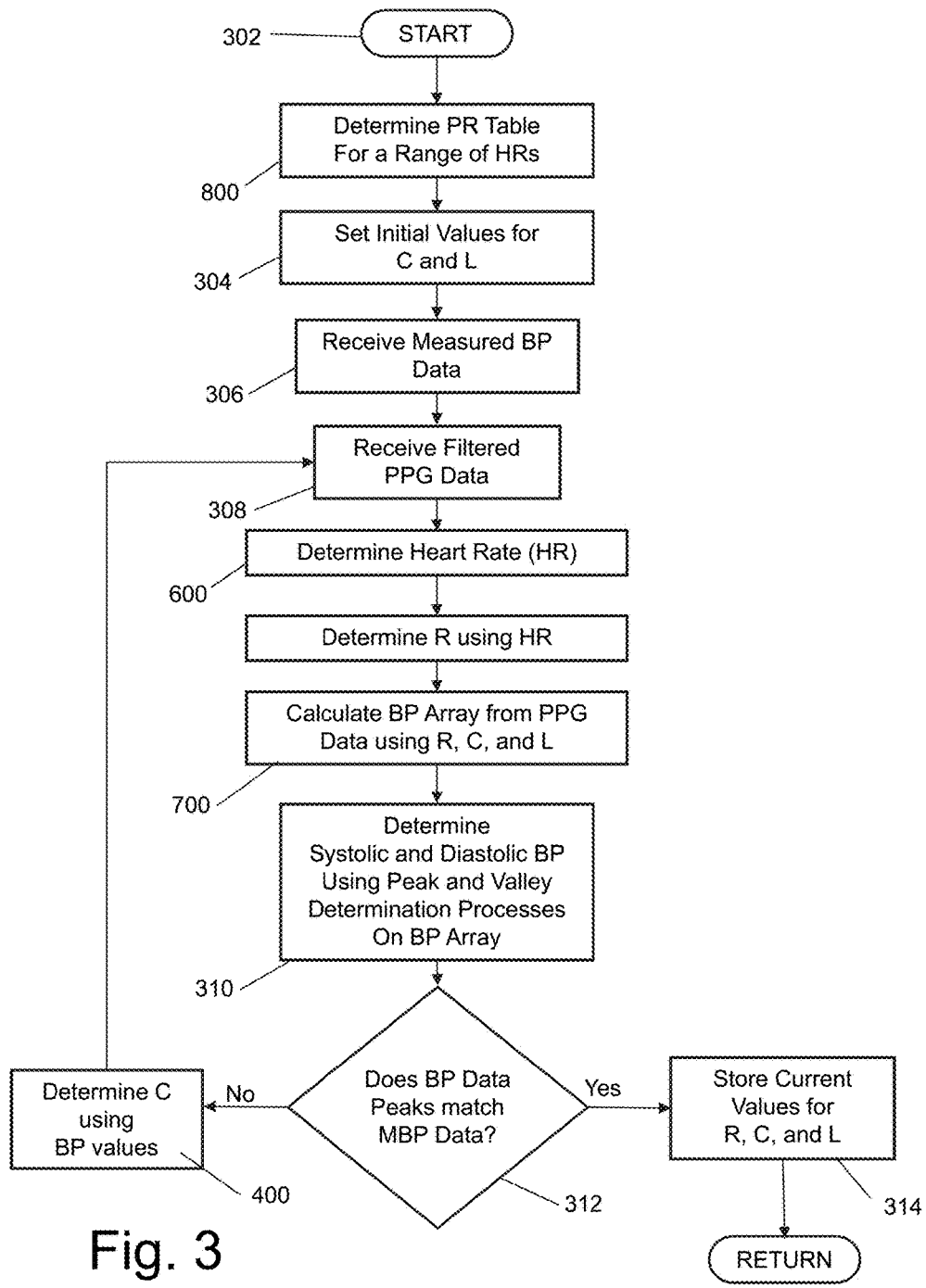
FIG. 3 is a flowchart representing a calibration sub-process which may be implemented by the process illustrated in FIG. 2.

The coefficient values for L, R and C of equation (2) (above) for an individual user may also be determined from analyzing and correlating the PPG signal curve of FIG. 9A to the blood pressure curve of FIG. 9B, then correlating the curves back to the fundamental BP model as expressed by equations (1) and (2) above. One such numerical method for determining the coefficient values L, R, and C is presented in FIG. 3 as sub-process 300.

The process 300 starts at step 302 which begins the subprocess 300 and then flows to step 800. Step 800 determines a range of values for the vascular or peripheral resistance coefficient ("R"). Although the R is unique for every individual, in certain embodiments, R can be determined empirically for a group of individuals where the R varies according to the placement of the system 100 on the user and the heart rate of the user.

In one embodiment, R may be approximated by retrieving a value from a lookup table wherein the data is derived from empirical testing for a particular heart rate. In another embodiment, a user could input statistically relevant information about the user, for instance, age, level of physical activity, BMI, medical history, and gender via a questionnaire application running on another computer device in communication with the system 100. In such an embodiment, R is thus selected from additional lookup tables which have empirical data based on additional factors, such as age, level of activity, BMI, medical history, and gender.

In certain embodiments, lookup tables may generated by a sub-process (e.g. sub-process 800) which generates a Peripheral Resistance lookup table using curve fitting techniques to produce the equivalent of empirical data for a wide range of heart rates likely to be encountered. Specific details regarding the generation of the Peripheral Resistance lookup table are discussed below in reference to FIG. 8. In other embodiments, the Peripheral Resistance lookup table (or other tables relating to the Peripheral Resistance lookup table) may be stored in the memory 120 as discussed above. As a result, in certain embodiments, for any given heart rate, the corresponding PR or R value may be determined from the lookup table.

Numerical methods may be used to determine coefficient values to be used in blood pressure estimates, such as C and L. In certain embodiments, these initial parameters are set to predetermined values, then mathematical processes are iterated until the coefficient values are within an acceptable tolerance or criteria. Specifically, in step 304, initial coefficient values are set for C and L. For instance, C may be set to 10 and L may be set to zero.

In order to proceed with the next step in the calibration process, blood pressure data ("BP" data) of the user may be measured by an external blood pressure reference device and received by the system (step 306) via a user inputting blood pressure values or BP data via an interface or external program application in communication with the system 100 (such as a application running on a phone). The received BP data may be a measured Systolic Blood Pressure ("SBP") and the measured Diastolic Blood Pressure ("DBP") values.

In one embodiment, a blood pressure reference device, such as an Arterial Line Transducer or a cuff blood pressure measuring device may be used to obtain Blood Pressure data ("BP data") from the blood pressure reference device. In one embodiment, the Blood Pressure Data is input into the system by the user. After the BP data is received by the system, as will be explained below, the BP data may be correlated to a BP curve, which may then be correlated to the received PPG signal curve 315 to determine coefficient values.

In step 308, the user can place the system 100 at a predetermined location such as a finger or ear lobe so that the system 100 can begin generating PPG data. Essentially, steps 208, 210, 212 as explained above are repeated to obtain a new signal (e.g., a series or set of filtered and quantized data sampling points).

Using the new data points in the Q array, the sub-process 600 may be implemented again to determine the heart rate "HR" for the new data sampling points. In certain embodiments, this is performed by the sub-process 600 which looks for peaks in the PPG data array. Specific details regarding the determination of the heart rate (HR) are discussed below in reference to FIG. 6.

In certain embodiments, at step 309, the value for the HR is used to determine "R." In certain embodiments, the HR value is used in conjunction with the lookup table created in step 800 above to select (interpolate/extrapolate) R. As discussed above, in other embodiments, R may also be a function of specific values derived from a user's profile.

In step 700, a subprocess is implemented which calculates a blood pressure curve or function using the current values for the HR, C, L, and R. Additional details regarding the subprocess 700 are discussed with reference to FIG. 7 below.

In step 310, depending on the orientation of the data in the Q array, a Peak Detector may be used to determine systolic BP (SBP) and Valley Detector process determines the diastolic BP (DBP). In one embodiment, the peak and valley detectors uses a least squares fit method to check the shape of the received signal against a predetermined quality threshold in each case. In yet other embodiments, class libraries from programming environments (such as LabView) may be used for functions such as peak detection, derivatives, integrals, queuing, and bandpass filtering.

In step 312, a check is performed to determined if the calculated SBP and DBP values determined in step 310 matches (e.g., falls within an acceptable tolerance) the measured SBP and DBP values determined in step 306 above. If the calculated SBP and DBP values match the measured SBP and DBP values, the values for C, L, and R are determined to be good values and these are stored for later use (step 314) and the process returns to the main process 200 in step 316.

On the other hand, if the calculated SBP and DBP values do not match the measured SBP and DBP values, the process flows to step 400, where a subprocess is implemented to determine a more accurate C value. (As will be explained below with reference to FIG. 4, the subprocess 400 may call an additional subprocess to determine a more accurate L coefficient value). Thus, upon completion of the subprocess 400, new values for C (and possibly L) are calculated.

The process then flows back to step 308 where steps 308 through 310 are repeated with the newly calculated values for C (and possibly L). At step 312, the calculated SBP and DBP values are again compared to the measured values for SBP and DBP. If the comparison is not within the predetermine tolerance, steps 400 through 312 are iterated until values for C, R and L are found which cause the calculated SBD and DBP to match the measured SBD and DBP.

As discussed above, C is used in Equation (2) (above):

$$u = \int \left( R\frac{di}{dt} + L\frac{d^2i}{dt^2} + \frac{i}{C} \right) dt \quad (2)$$

The variable "u" represents blood pressure. The values of u are known at the peaks 930 and valleys 932 along the BP curve 335 in FIG. 9B when the measured SBP and DBP values are imposed on the BP curve 935. Thus, the average blood pressure may be calculated according to the following equation:

$$\underline{u} = DBP + \frac{SBP - DBP}{2} \quad (3)$$

However at this point values for R and L are not known in Equation (2). To determine C, one could solve the Equation (2) for an averaged pressure (which can be determined by equation (3) and when the first R and second L derivatives are equal to 0 which conveniently happened to correspond to the peaks on the BP curve 335.

Thus, thus when the first and second derivatives are equal to zero, Equation (2) becomes equation (4) below. Equation (4) then can define the relationship between C and the average blood pressure.

$$u = \frac{1}{C} \int i \, dt \quad (4)$$

Numerical methods may be used to solve Equation (4). One such numerical method estimate for determining C is illustrated in FIG. 4.

Figure 4:
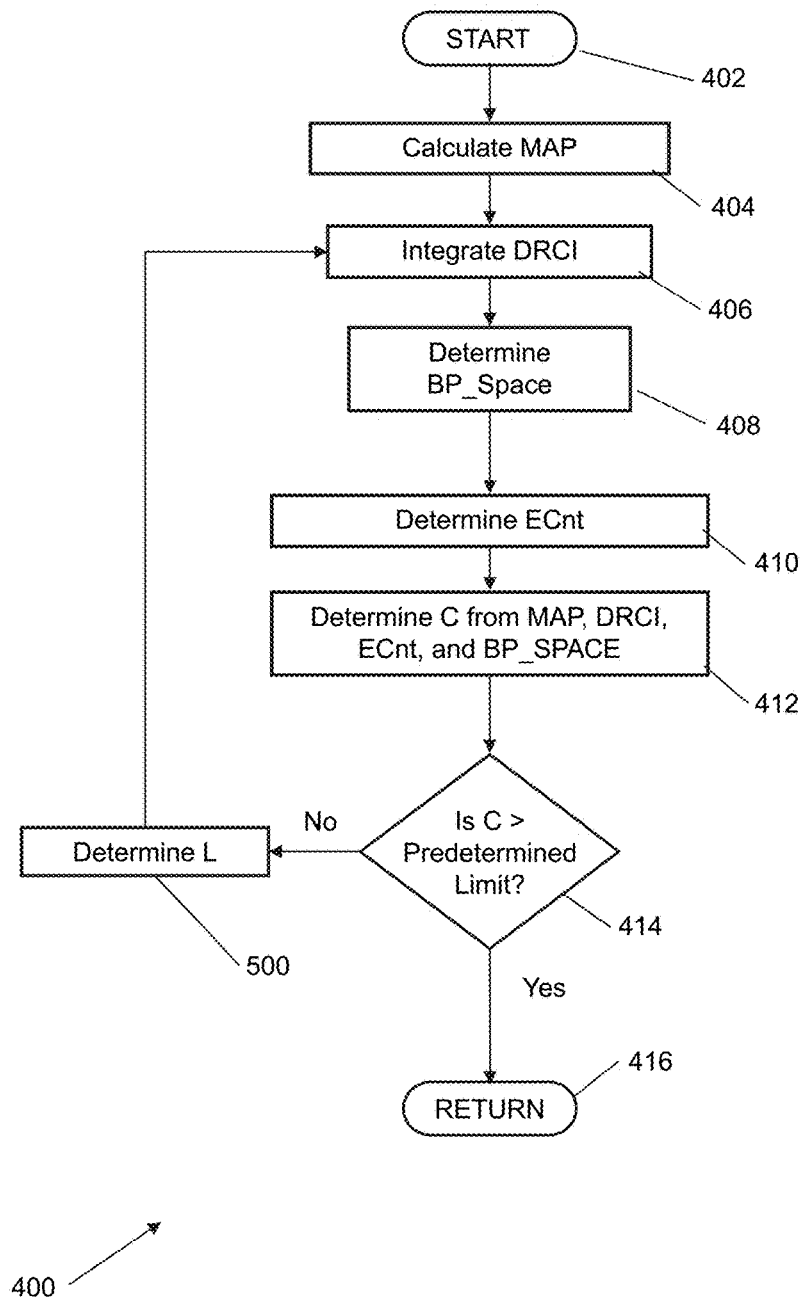
FIG. 4 is a flowchart representing a "C" determination sub-process.

Turning now to FIG. 4, there is the process 400 for estimating the C coefficient. The process starts at step 402 and flows to step 404 where the mean arterial pressure or "MAP" is estimated. In certain embodiments, the value for MAP may be calculated according to the following formula:

$$MAP = \frac{2MDBP + MSBP}{3} \quad (5)$$

where:
 MDBP—is the measured diastolic blood pressure (DBP) received from a reference device in step 306 above, and
 MSBP—is the measured systolic blood pressure (SBP) received from a reference device in step 306 above.

In step 406, a relationship or function named DR_CI is integrated or scanned to determine the average value of each DR_CI pair in the Q array according to the trapezoidal formula below:

$$\int_0^z DR\_CI = \sum_{z=0}^{\infty} \frac{|DR\_CI|_z + |DR\_CI|_{z+1}}{z} \quad (6)$$

In certain embodiments, the above equation (6) is solved as a continuous sum of definite integrals where b-a=1. The variable "a" may be set to zero when the devices is first turned and this process begins. On the other hand, "b" is the last value (whenever the device is turned off or otherwise force a restart of the process).

The function DR_CI correlates to the ability of the vascular system to allow the blood to flow despite of the discharge resistance (DR) of the system. In certain embodiments, DR_CI can be estimated according to the following formula:

$$DR\_CI = CI - Q \times DR \quad (7)$$

where:
 Q is a particular value of the array generated during step 308 above.
 DR is the Discharge Resistance. In certain embodiments, DR is an empirical number based on the user's profile values (such as sex, age, height, weight, BMI and other factors). In certain embodiments, the value may be estimated as a fixed value, such as zero.

In equation (7) above, CI is a parameter correlating the ability of the vascular system to promulgate the blood to keep the flow. It can be represented mathematically by:

$$CI = I_{nd} \times \frac{Q}{C} \quad (8)$$

where:
 $I_{nd}$ relates to the inductance of the vessels. $I_{nd}$ can be estimated from the following formula:

$$I_{nd} = \frac{\Delta R}{\Delta t} \times L$$

where L is the current value of L at this step in the process. Initially, L is defined as zero.

In certain embodiments, R can be estimated according to the following formula:

$$R = \frac{\Delta Q}{\Delta t} \times PR \times VR \qquad (9)$$

where:

$\Delta Q$ is equivalent to dQ/dt where dt is 1.

PR is the value from the PR Lookup Table for the particular heart rate at this interval.

VR is the Variable Resistance. In certain embodiments, the VR can be estimated based on values from a user's profile (such as sex, age, height, weight, BMI and other factors). In certain embodiments, the value may be an estimated fixed value, such as 0.015.

In step 408, a coefficient BP_SPACE is determined. BP_SPACE is an empirical coefficient that correlates to the placement of a sensor on the body. For certain embodiments using finger placement devices, BP_SPACE may be 4.

In step 410, a counter $EC_{nt}$ is employed as a check on good signals representing heart beats. Beats are checked against predetermined criteria. If the beats do not meet these criteria, they are discarded.

In step 412, the compliance coefficient can be estimated according to the following formula:

$$C = \frac{\int DR\_CI}{\frac{EC_{nt}}{MAP}} \times 2^{BP\_SPACE} \qquad (10)$$

where the coefficient values have been determined in steps 404 through 410 discussed above.

In step 414, a check is performed on the value of the C coefficient to determine if the current value is within a predetermined quality limit. If the calculated C coefficient is within this predetermined limit, the values for C, L, and R are determined to be good values and the process 400 returns to step 308 of the process 300 as describe above (with the new values for C and, in some embodiments, L and R). On the other hand, if the current value for C is greater than the predetermined quality limit, the process flows to step 500 where a subprocess estimates the coefficient value for L. Once the process 500 determines a new value for L, steps 406 through 412 are repeated using the new value for L. This loop (of steps 406 to 500) is iterated until C falls within the predetermined limit and, then returns to the subprocess 300 in step 416.

In one embodiment, L is determined by a search method, sweeping the value of L from 1 to 30 on an entire spectrum of predefined heart rates. The search process runs until the following criteria fails:

$$SBP_j \geq \int_0^T \left( L_k \frac{d^2 i}{dt^2} + R \frac{di}{dt} + \frac{i}{C} \right) dt \qquad (11)$$

Then the inductance can be extracted from a condition. In other words, if Lk meets the condition of equation (11), $L_k$ is used. If $L_k$ does not meet the condition of equation (11), $L_{k-1}$ is used.

In another embodiment, the L determination process includes three primary steps: (1) Inductance generation, (2) Pulse Pressure Calculation, and (3) Inductance Extraction/Definition.

The inductance may be generated according to the following:

$$L_i = L_{i+1} + L_{scale} \text{ if } SC_i \text{ is High and } K = L_{hold}; \text{ otherwise } L_{i-1} \text{ if otherwise} \qquad (12)$$

where i is the number of the pulse identified with the PPG signal, K is a counter that indicates the number of pulses that are used or considered in the calculation of L. The maximum value for K is the $L_{hold}$ or LHOLD which may be reset to 0 after reaching the maximum value. As explained below LHOLD is a variable representing a predetermined number of valid pulses or heart beats.

In order to determine L, a valid pulse pressure is selected according to the following conditions:

$$PPV_i = \text{high if } PP_m + PP_{tol} \geq PP_c \geq PP_m - PP_{tol}; \text{ or low if otherwise} \qquad (13)$$

Then the signal of the selected L can be generated as:

$$Ls_i = L_i \text{ if } PPV_i = \text{High, } 0 \text{ if } PPV_i = \text{Low} \qquad (14)$$

L can then be calculated as:

$$Lc = \frac{\sum Ls_i}{K} \qquad (15)$$

where

K=K+1 if PPVi is High, and K if PPVi is Low.

This process continues until the L reaches its maximum value, which in certain embodiments, may be 50 or PP≥3/2 PPM. In the final step of the process, the arithmetic average of all valid values of $L_i$ is calculated.

Figure 5A:
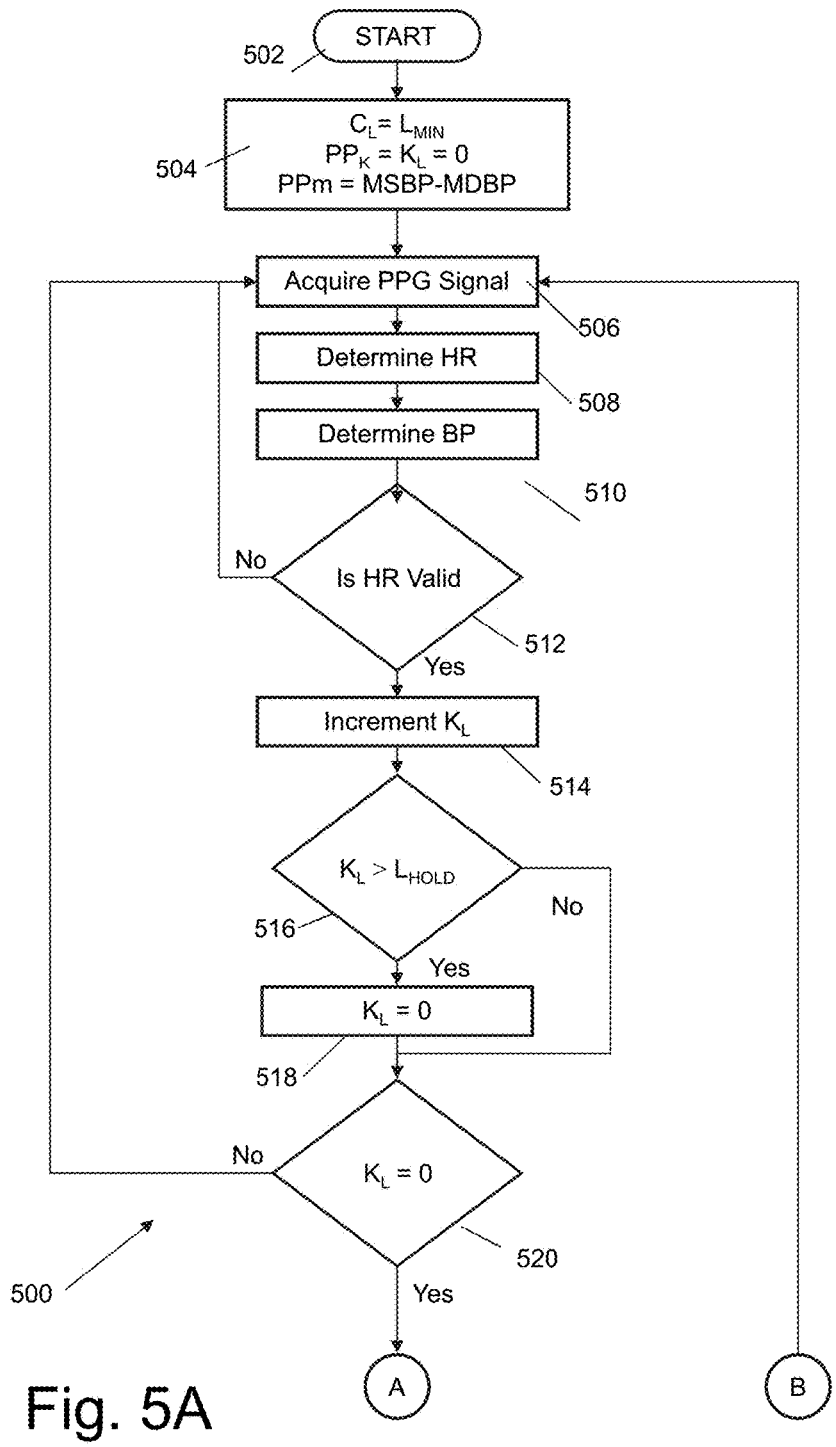
FIG. 5A is a flowchart representing a first portion of an "L" determination sub-process.
Figure 5B:
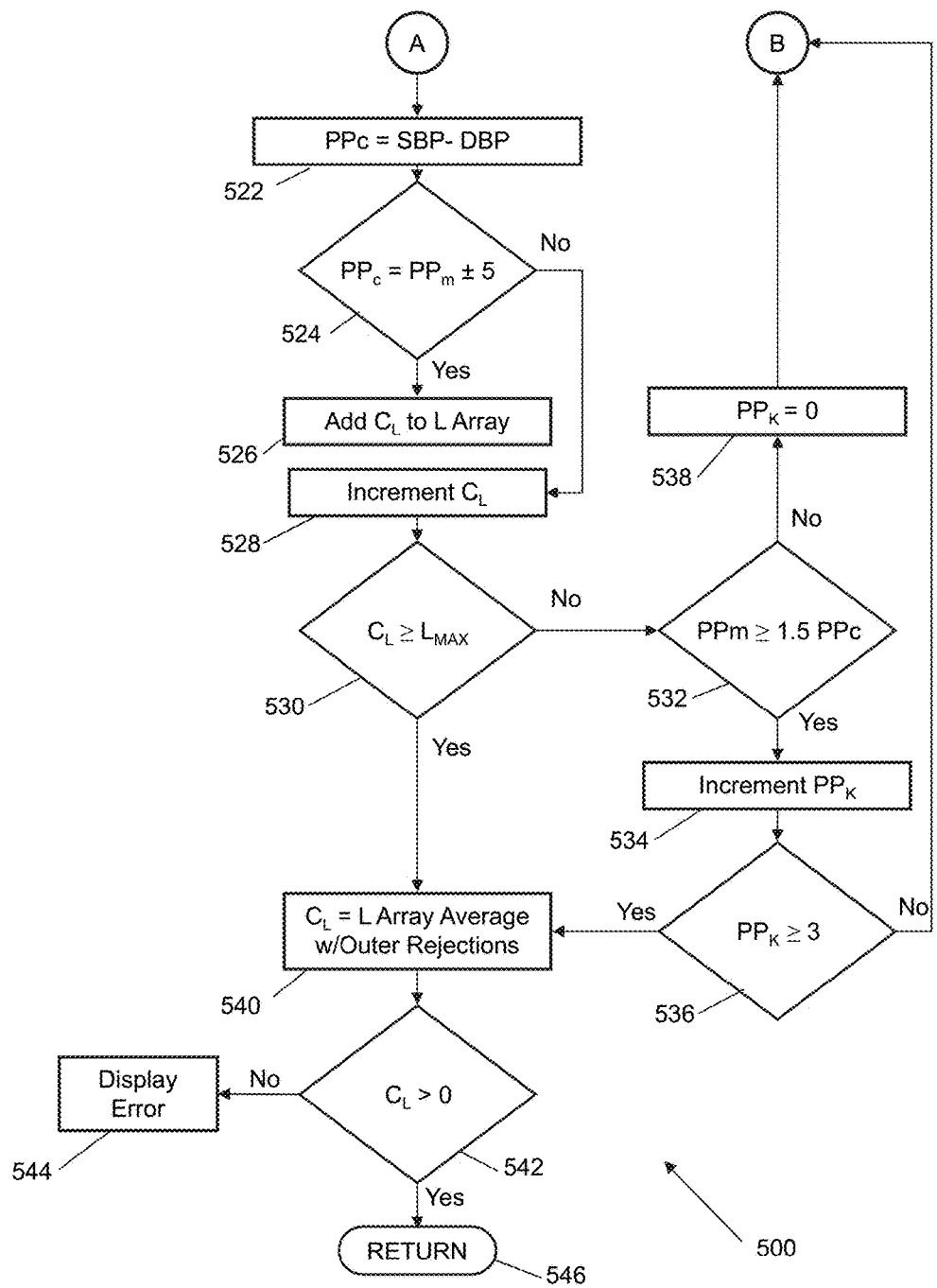
FIG. 5B is a flowchart representing a second portion of an "L" determination sub-process.

An alternative L determination process 500 is illustrated in FIGS. 5A and 5B. The process 500 starts at step 502 and flows to 504 where initial values are set. For instance, the current determination of L or (which in certain embodiments may be represented by a counter "CL") is set to be LMIN. In certain embodiments, LMIN may be zero. Counters PPK and KL are also set to zero and the measured pulse pressured is determined. The measured pulse pressure (PPM) may be determined by the following formula:

$$PPM = MSBP - MDBP \qquad (16)$$

where: MSBP is the measured systolic blood pressure and MDBP is the measured diastolic blood pressure determined in step 306 described above.

In the process 500, the counter CL is incremented for every valid pulse or heart beat which may be tracked by LHOLD. At the beginning of the process CL is set to zero. At the end of the process, CL is set to an average of the CL values that meet a predetermine criteria for good pulse signals. To track the CL values, an array may be used and stored in the memory 120. A particular cell of interest in the array, such as Li may be the ith item in an L array of CL values. (The L Array is a single dimensional array of all of the CL values tried during the L determination process (CL candidates) that produces a pulse pressure within an acceptable range when compared to the measured pulse pressure.)

The process 500 runs on the current filtered PPG signal (or data points) being received from the PPG system. Consequently, the filtered PPG signal is received in step 506. A heart rate determination routine, such as the HR process 600, is performed on the received PPG signal to determine the current heart rate in step 508. In some embodiments, a blood pressure estimation routine, such as the BP process 700 is performed on PPG signal to determine blood pressure.

In certain embodiments, the accuracy of the L determination sub-process 500 depends on a minimum number of valid heart pulse signals. In steps 512 through 520, the system waits until a predetermined number of valid beats (or pulse signals) have been received. The valid beats are not necessarily consecutive. So, a counter KL may be incremented, tested and reset if to 0 if the counter goes over a predetermined number of valid beats (e.g., L_HOLD).

In step 512, the heart rate is tested against predetermined criteria to determine if the heart rate appears to be valid. If the heart rate does not appear to be valid, the process loops back to step 506 where a new signal is received. If the heart rate appears to be valid, the counter KL is incremented in step 514 and the process flows to step 516.

In step 516, the counter KL is checked against the variable LHOLD (which is a predetermined number of valid beats, for instance two). If KL greater than LHOLD the process flows to step 520. If KL is less than LHOLD, the process flows to 518 where the counter KL is reset to zero.

In step 520, the process loops back to step 506 if KL is equal to zero, otherwise it has been determined that the system has enough heart rate signals to continue to the next step. Connecting point "A" of FIG. 5A connects to connecting point "A" of FIG. 5B and is meant to signify that the process continues on to FIG. 5B and flows to step 522.

At step 522, the calculated pulse pressure ("PPC") may be determined from the most recent SBP and DBP determinations from step 510 above according to the following formula:

$$PPC = SBP - DBP \quad (17)$$

In step 524, a check is performed to determine if the calculated pulse pressure PPC is within a predetermined tolerance (e.g., within 5 points) of the measured pulse pressure ("PPM"). If yes, then in step 526, the current value for CL is added to the L Array as a good candidate for L. If not, then the process flows to step 528 where the CL counter is incremented.

In step 528, CL maybe incremented by a user adjustable variable Lscale. In certain embodiments, Lscale is set be default to be the value 2.

In step 530, a check is performed to see if CL is greater or equal to Lmax, which in certain embodiments may be set to 50. If CL is less than Lmax, the process flows to step 532. In step 532, a check is performed to see if the measured pulse pressure PPM is greater than 1.5 times the calculated pulse pressure PPC. If yes, the process flows to step 534 where the counter PPK is incremented. On the other hand if not, the process flows to step 538 where the counter PPK is set to zero. The process then loops back to step 506 where a new PPG signal is acquired (which is shown graphically through the connecting points "B" on FIGS. 5A and 5B).

After the PPK is incremented at step 534, the process flows to step 536 where a check is performed to determine if PPK is greater than a predetermined maximum number of consecutive pulse pressures that meet the condition of in 532. If yes, then the process flows to step 540. Otherwise, the process flows back to step 506 above where a new PPG signal is acquired. The check of step 532 and the counter PPK are used to exit the L calibration process early if it is determined that the process has gone past the correct values for CL but not yet reached LMAX.

At step 540, the value of CL is set. Generally, the value of CL is the average of previously determined CL values in the L Array that meet the predetermined criteria (candidate CL values) in step 524 above. CL may be expressed as:

$$C_l = \sum_{i=0}^{n} Li[|L_i - m(l)| < L_{Tol}] \quad (18)$$

where:
Li is the ith item in the L array of candidate CL values.
m(I) is the mean of the L array of candidate CL values.
$L_{TOL}$ is the tolerance for the outliers—which may be determined empirically. In certain embodiments, it may have a value of pulse or minus 10.

The brackets in the above formula (18) indicate a conditional sum in Iverson notation. In other words, the Iverson bracket converts a Boolean value to an integer value through the natural map false=0, true=1 which allows counting to be represented as the summation.

The process then flows to step 542, where a check is performed to determine if the CL is greater than zero. If yes, the value of L is set to CL and the sub-process 500 returns (at step 546) to the parent sub-process 400 or any other processes which called this sub-process. If CL is less than zero, an error message is displayed at step 544.

Figure 6:
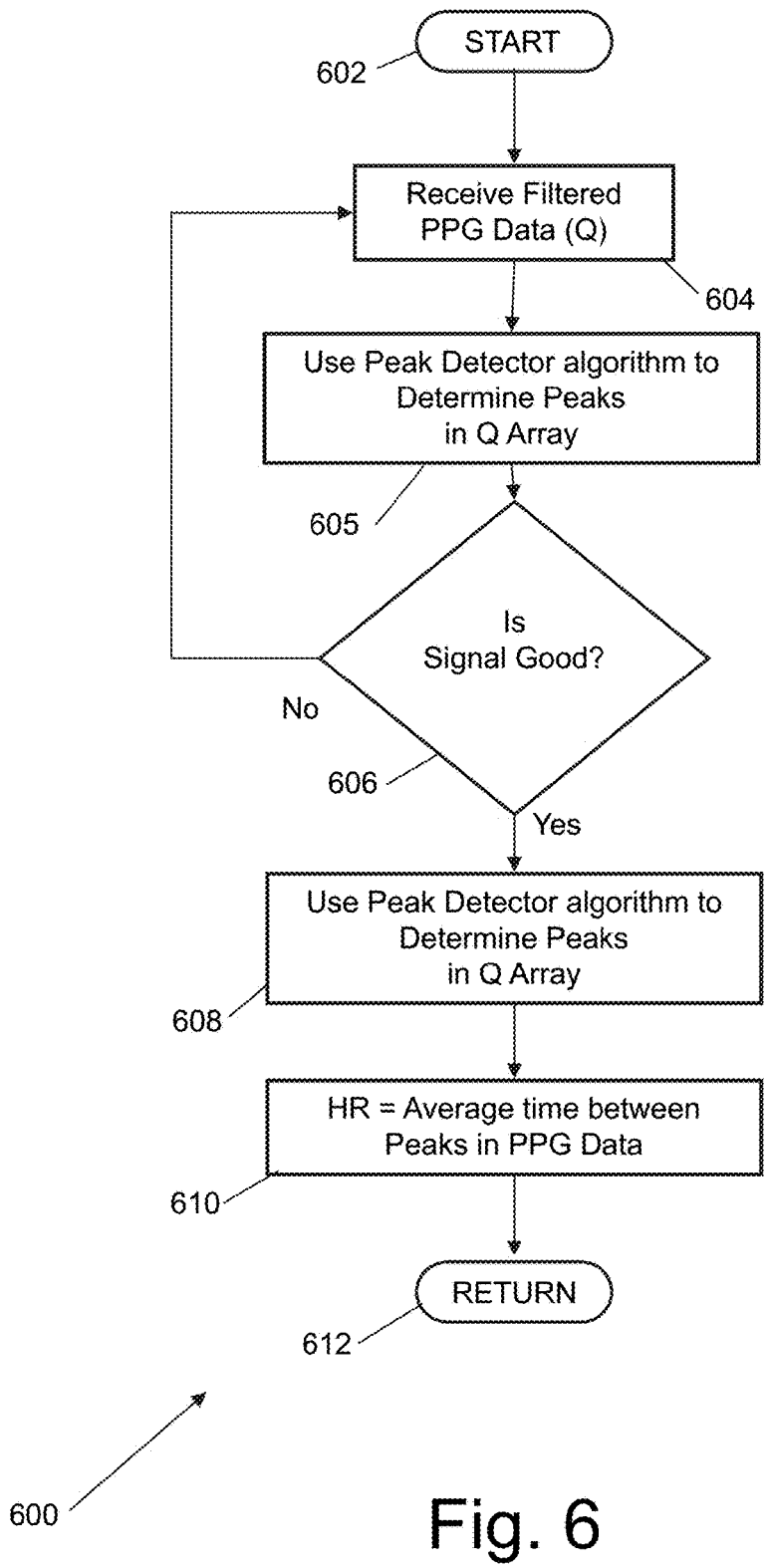
FIG. 6 is a flowchart representing a heart rate determination sub-process.

Turning now to FIG. 6, there is a flow chart illustrating one method 600 for determining the heart rate. The process starts at step 602 and flows to step 604 where filtered data points from the PPG system or sensor is received and may be stored in a set of cells in memory or "Q Array."

The process then flows to step 605, where a peak/valley detector routine is applied to the PPG signal to determine general peaks and valleys in the signal which are represented by a set of filtered data points in an array or table such as the Q Array (e.g., the peak 906a of the curve 915 of FIG. 9).

The process then flows to step 606 where a signal check is performed. If the received signal does not meet a predetermined criterion, the process flows back to step 604 where a new signal is obtained and the steps 604 to 606 are repeated. On the other hand, if the signal meets the predetermined criteria the process flows to step 608. In certain embodiments, the signal check may be based on comparing the last 2 valleys with the current peak on the 0.5 to 4.0 Hz bandpass filtered second stage (OpAmp2) signal. A "valid" value is updated for each peak and may be used as a signal check by this and other routines until the next peak is encountered. In certain embodiments, the technique basically turns off most processing for at least one heart beat and turns it on again if it gets at least one good heartbeat. In certain embodiments, sequential peaks are checked, where a second peak has to be between 0.333 and 1.111 times the current or first peak in the window.

In certain embodiments, the process then flows to step 608, where an additional peak/valley detector routine is applied to the Q Array to determine peaks and valleys in the signal (e.g., the peak 906a of the curve 915 of FIG. 9). In certain embodiments; this Peak/Valley detector may be a quadratic least squares process peak detector using consecutive values (e.g., three) of the filtered Q waveform array.

Once the peaks or valleys have been determined in step 608, the individual pulse widths between the peaks (e.g., 910a and 910b of FIG. 9) may be determined in step 610, for instance, by just determining the time between peaks. Of course, the time between the peaks correlates to the heart rate.

A series of pulse widths may be averaged for display or storage in step 610 or the instantaneous heart rate returned when the procedure returns (step 612) to the procedure that called the process 600.

Figure 7:
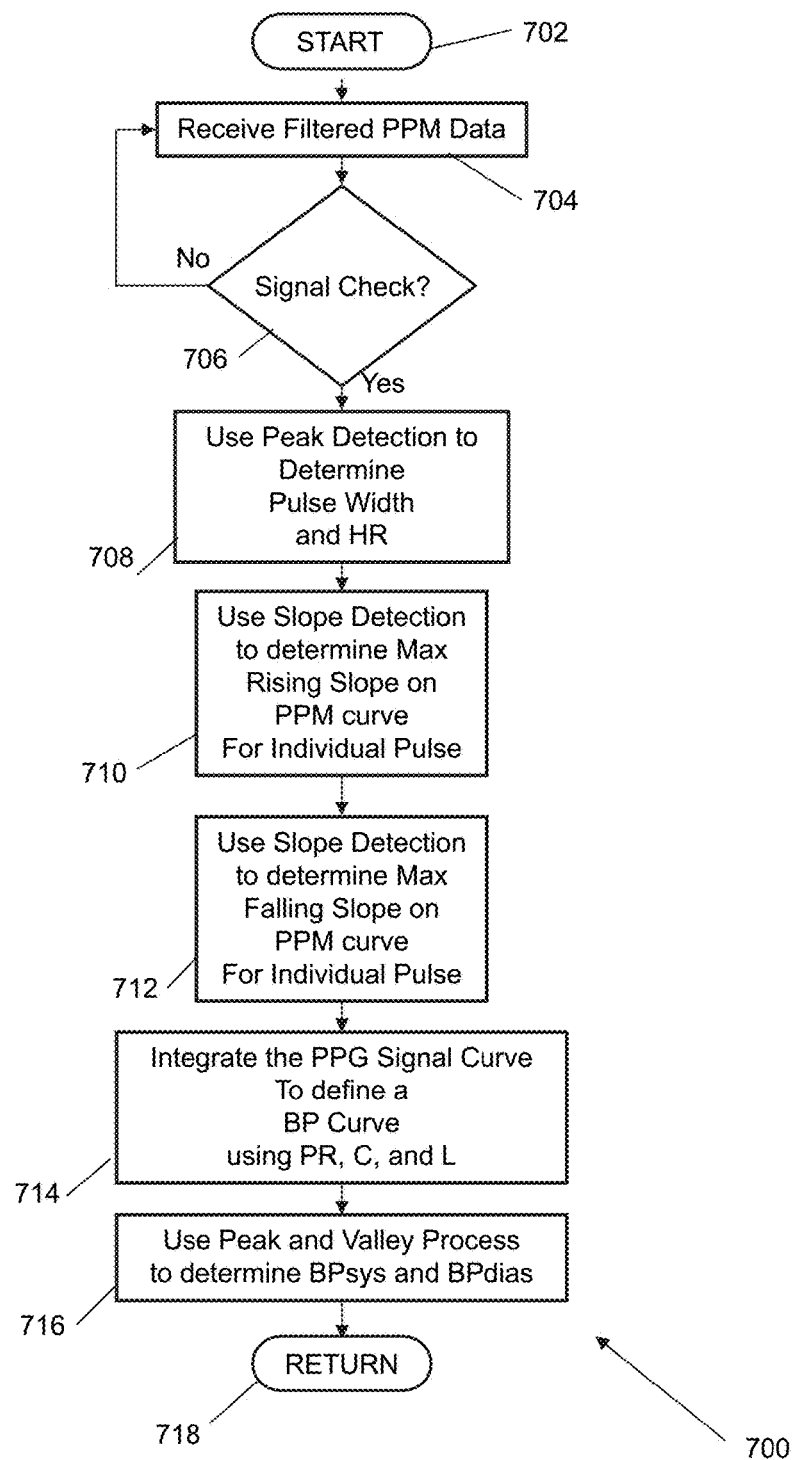
FIG. 7 is a flowchart representing a blood pressure determination sub-process.

Turning now to FIG. 7, there is a flow chart illustrating one exemplary process 700 for determining blood pressure. The process 700 begins at step 702 and flows to step 704 where filtered data points from the PPG system are received.

In step 706 a signal check is performed to check the shape of the waveform. In certain embodiments, the signal check step uses the last two valleys and the current peak on the 1.75 to 4.0 Hz bandpass filtered signal. In other words, if the current peak minus next to last valley is between 33 to 111% of current peak minus last valley, the shape of the signal is determined to be good and the process continues to step 706. If the signal check fails, the process loops back to step 704 to acquire more data from the PPG system.

Using the received data points, in step 708, the sub-process 600 may be implemented again to determine the heart rate "HR" for the new data sampling points. In certain embodiments, this is performed by the sub-process 600 which looks for peaks in the PPG data array or Q array. Specific details regarding the determination of the heart rate (HR) are discussed above in reference to FIG. 6.

In step 710, the first and second derivatives on the rising point data may be determined. In some embodiments, this can be accomplished with a Slope Detector routine or function to determine Max Rising Slope for Individual data points under analysis. Although, any slope detector method may be employed, in certain embodiments, finite difference formulas may be used to determine the slope of the secant line through adjacent points in the data.

In step 712, the first and second derivatives on the falling point data may be determined. In some embodiments, this can be accomplished with a Slope Detector routine or function to determine Max Rising Slope for Individual data points under analysis. Although, any slope detector method may be employed, in certain embodiments, finite difference formulas may be used to determine the slope of the secant line through adjacent points in the data.

In step 714, the PPG signal curve may be integrated as discussed above. In one embodiment, the BP pressure curve is determined by applying the following formula to each pair of values (a, b) of the received signals.

$$P = (b-a)\left[\frac{f(a)-f(b)}{2}\right] \quad (19)$$

The function f(x) used above in equation (19) is $$f(x)=L+C\_DIV-Q\times DR \quad (20)$$

where:
DR is the discharge resistance. In certain embodiments, this is a fixed value based on empirical data, and
$C\_DIV=Q/C_C$ where $C_C$ is the coefficient of C derived from the C determination process.
In equation (20) above, L is $$L = \frac{\Delta R}{\Delta t_{HR}} \times C_L \quad (21)$$

Where:
$C_L$ is the current value of L—which is either the default value for L or the value of L determined from the L calibration sub-process 500 discussed above.

$\Delta R=R(b)-R(a)$ $\Delta t_{HR}$=the HR interval
$C\_DIV=Q/C_C$ where $C_C$ is the coefficient of C derived from the C determination sub-process 400 discussed above.
In equation (21) above, R is $$R = \frac{\Delta Q}{\Delta t} \times PR \times VR \quad (22)$$

where:
$\Delta Q=Q(b)-Q(a)$ where a and b are adjacent values of the Q Array
$\Delta t$=is the time interval of the Q Array sampling or 1.
PR—is the value from the lookup table for the current HR.
VR—is a variable resistance estimate for an average person.

Once enough blood pressure data points have been calculated (or data points corresponding to blood pressure), in step 716, peak and valley detectors are used on the BP data points to determine SBP and DBP. In one embodiment, the peak and valley detectors uses a least squares fit method to check the shape of the signal against a threshold in each case.

In step 718, the process returns to the procedure calling the process 700.

Figure 8:
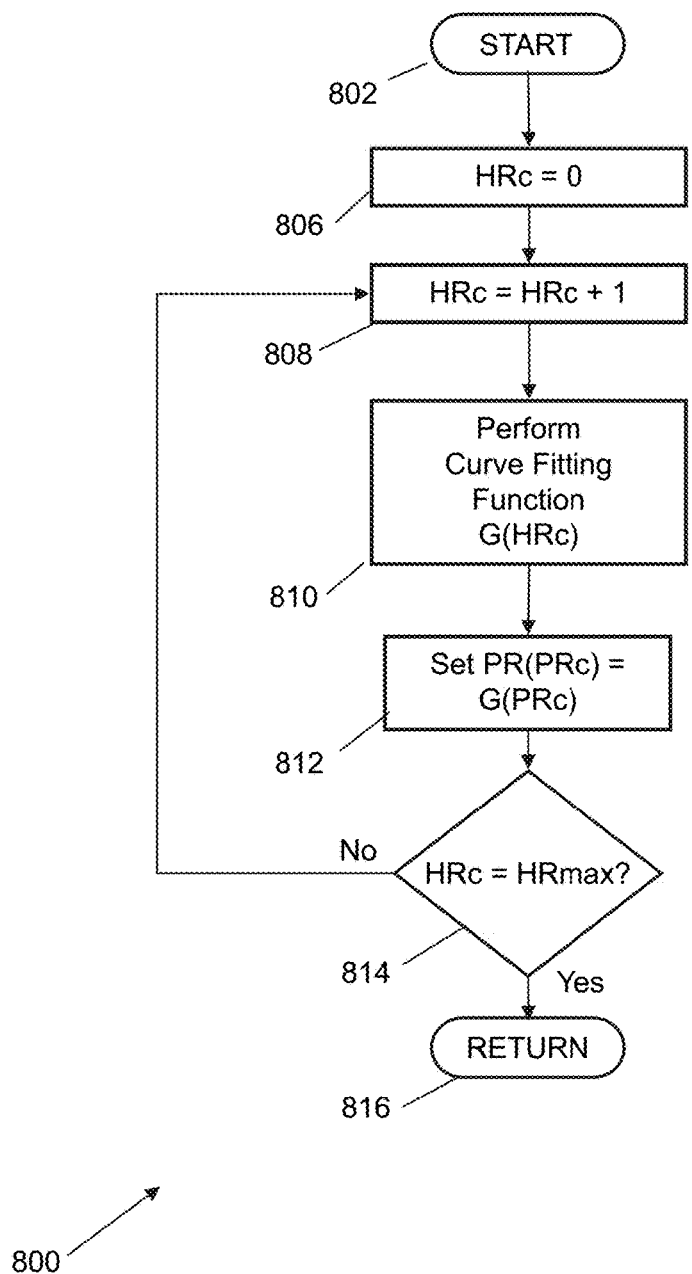
FIG. 8 is a flowchart representing a sub-process for populating a peripheral resistance table or array based on heart rates.

Turning now to FIG. 8, there is illustrated one sub-process 800 for populating a peripheral resistance table array PR(HR) based on heart rates. In certain embodiments, the sub-process 800 is called from the calibration sub-process 300 as discussed above. In certain embodiments, the lookup table or array PR(HR) is populated for likely values of Heart Rates ranging from 0 to 159. Empirical data indicates a correlation between the position of the sensor, the heart rate, and the peripheral resistance ("PR"). As the position of the sensor is known for a particular device, curve fitting functions can be performed to populate a one dimensional array correlating HR to PR from empirical data. Thus, for any given HR, the correlating PR value can be determined via the lookup table PR(HR).

The process starts at step 802 and flows to step 806 where a counter "$HR_C$" or "HRC" for the populating the PR table is initially set to zero. The process then flows to step 808 where the counter HRC is incremented by 1.

In step 810, a curve fitting function is executed using the current value of the counter HRC or "x". In one embodiment, the curve fitting function used to generate the PR values is:

$$G(x)=(g(\lfloor x \rfloor)\pm x-\lfloor x \rfloor)\times(g(\lfloor x \rfloor+1)-g(\lfloor x \rfloor)) \quad (23)$$

where:

$$g(x) = \frac{e^{e^{((m(x))\times((m(x)+0.0075))}}}{300},$$

and $$m(x)=HRc\times 0.0075+0.01$$

Thus, for any given HRC value, a corresponding G(HRC) value can be determined by running the HRC value through the above equation. In step 812, the corresponding cell for the HRC is set to this value.

In step 814, a check is performed to see if the HRC has reached the maximum value for the curve fitting data. In one embodiment, this maximum value is 159. If HRC has not reached the maximum value, the process loops back to step 808, where HRC is incremented by one and steps 810 through 814 are repeated. If the HRC has reached the maximum value, step 816 is executed which returns the sub-process 800 back to the parent process calling this routine (i.e., the calibration sub-process 300).

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

The invention claimed is:

1. A method of continuously monitoring blood pressure, the method comprising:
    (a) retrieving previously stored values for inductance (L) and compliance of the cardiovascular system (C);
    (b) receiving a photoplethysmographic (PPG) signal for each pulse or for a given time period;
    (c) filtering the received PPG signal to produce a clean PPG signal;
    (d) determining the heart rate;
    (e) determining the peripheral resistance using the heart rate and a profile-based lookup table;
    (f) calculating the blood pressure using the clean PPG signal, the peripheral resistance, L and C; and
    (g) determining the systolic and diastolic blood pressure.

2. The method of claim 1, further comprising performing a calibration sub-process to determine L and C for each individual user.

3. The method of claim 1, further comprising repeating steps (a) through (g) for each predetermined time period.

4. The method of claim 1, further comprising repeating steps (a) through (g) for each pulse of a user.

5. The method of claim 1, further comprising storing the systolic and diastolic blood pressure in a memory.

6. A system for continuously monitoring blood pressure, the system comprising:
    a light source;
    an optical sensor positioned to receive reflected light from the light source;
    a signal processing unit adapted to receive an electrical signal from the optical sensor and configured to output a clean digital signal;
    a microprocessor in communication with the light source, the signal processing unit, a memory and a computer/wireless interface, the microprocessor having instructions for:
        (a) retrieving previously stored values for inductance (L) and compliance of the cardiovascular system (C);
        (b) receiving a photoplethysmographic (PPG) signal for each pulse or for a given time period;
        (c) filtering the received PPG signal to produce a clean PPG signal;
        (d) determining the heart rate;
        (e) determining the peripheral resistance from thea selected profile-based lookup table using the heart rate;
        (f) calculating the blood pressure using the clean PPG signal, the peripheral resistance, L and C; and
        (g) determining the systolic and diastolic blood pressure.

7. The system of claim 6, further comprising performing a calibration sub-process to determine L and C for each individual user.

8. The system of claim 6, further comprising repeating instructions (a) through (g) for each predetermined time period.

9. The system of claim 6, further comprising repeating instructions (a) through (g) for each pulse of a user.

* * * * *